United States Patent
Popp et al.

(10) Patent No.: US 6,433,024 B1
(45) Date of Patent: Aug. 13, 2002

(54) TOPICAL ANTI-ACNE COMPOSITION

(76) Inventors: Karl F. Popp, 1775 Duck Pond Rd., Schodack Landing, NY (US) 12156; Brent D. Stiefel, 8400 School House Rd., Miami, FL (US) 33143

( * ) Notice: Subject to any disclaimer, the term of this patent is extended or adjusted under 35 U.S.C. 154(b) by 0 days.

(21) Appl. No.: 09/567,302

(22) Filed: May 8, 2000

(51) Int. Cl.⁷ .................. A61K 31/075; A61K 7/00; A61K 9/00; A61K 7/135; A61K 39/245
(52) U.S. Cl. .................. 514/714; 514/859; 424/47; 424/62; 424/230.1
(58) Field of Search ................. 514/714, 859; 424/47, 62, 230.1

(56) References Cited

U.S. PATENT DOCUMENTS

| | | | |
|---|---|---|---|
| 3,535,422 A | 10/1970 | Cox et al. | 424/164 |
| 4,056,611 A | 11/1977 | Young | 424/62 |
| 4,105,782 A | 8/1978 | Yu et al. | 424/283 |
| 4,923,900 A | 5/1990 | De Villez | 514/714 |
| 5,958,984 A | * 9/1999 | Devillez | 514/714 |

OTHER PUBLICATIONS

Stiefel Laboratory Brochure, "Therapeutic Acne Wash Pan-Oxyl Bar", 1980.*

* cited by examiner

*Primary Examiner*—Marianne C. Seidel
*Assistant Examiner*—Brian-Yong S. Kwon
(74) *Attorney, Agent, or Firm*—Lott & Friedland, P.A.

(57) ABSTRACT

The present invention is directed towards a topical composition for the treatment of acne comprising water, an organic peroxide, an alpha hydroxy acid, a moisturizer, an isosorbide and a detergent. This invention also is directed to a method of making the composition of this invention. The method involves (1) heating water to between 60° C. and 70° C.; (2) adding a detergent base to the water and mixing the solution; (3) cooling the solution and adding an alpha hydroxy acid, an isosorbide and sodium pyrollidone carboxylate; (4) continuing to cool the solution to between 25° C. and 35° C. and then adding benzoyl peroxide and a preservative to the solution; (5) mixing and milling the product until smooth; and (6) adjusting the pH of the product to a pH of 3–5 with a base. This invention also is directed towards a method for treating a patient afflicted with acne by applying the composition of this invention to the affected areas of the patient's skin.

20 Claims, No Drawings

TOPICAL ANTI-ACNE COMPOSITION

TECHNICAL FIELD OF THE INVENTION

This invention relates to topical compositions for the treatment of acne.

BACKGROUND OF THE INVENTION

Acne and seborrhea are conditions of the skin characterized by an excessive flow of sebum from the sebaceous glands. Sebum reaches the skin surface through the duct of the hair follicle. The presence of excessive amounts of sebum in the duct and in the skin acts to block the continuous flow of sebum from the follicular duct. This produces a thickening of the sebum which becomes a comedone. Comedone formation is followed by hyperkeratinization of the follicular opening, completely closing the duct. The usual result is a papule, a pustule, or a cyst, often contaminated with bacteria which cause secondary infections.

Many topical therapeutic agents are used in the treatment of acne and seborrhea to prevent the blocking of the follicular duct, to reopen the duct once it has become blocked, to act against the infecting bacteria or the thickened sebum, or to provide combinations of each of these actions. Therapeutic agents which act to prevent the blocking of the follicular duct by promoting the removal or scuffing off of excess keratin are known as keratolytic agents. For example, the use of sulfur as a mild irritant to remove the horny layer of skin, and with it the debris clogging the follicular openings, is well known.

Several anti-acne agents are well known in the art. These include, for example, benzoyl peroxide, alpha hydroxy acids and detergents. Benzoyl peroxide is a colorless, odorless, tasteless crystalline solid that is stable at ordinary room temperatures. It is also a strong oxidizing agent which may be used as an antibacterial and keratolytic agent in the treatment of acne. Finely divided benzoyl peroxide often is incorporated in a cream or ointment for convenience in applying it to the skin. However, because of the powerful oxidizing properties of benzoyl peroxide, the inclusion of it in conventional ointment or cream bases often results in unstable compositions that display an unacceptably rapid loss in keratolytic potency. A stable benzoyl peroxide composition that is very effective in the treatment of acne and that has a projected shelf life of over eight years is described in U.S. Pat. No. 3,535,422 (the '422 patent) to Cox and Cuifo. The '422 patent describes a uniform dispersion of finely benzoyl peroxide particles in an emulsion of water and certain selected organic emollients. When the composition is applied to the patient's skin the water content of the emulsion evaporates leaving most of the organic emollients and the benzoyl peroxide particles on the surface of the skin near and in contact with the acne sites.

Benzoyl peroxide has been reported to be irritating to skin when applied at concentrations appropriate for the treatment of acne. The same is true of detergent-based anti-acne compositions. For example, detergent compositions based upon salts of lauryl sulfates (e.g., ammonium lauryl sulfate) are known to cause skin irritation.

Consequently, anti-acne compositions containing benzoyl peroxide and/or detergents often contain one or more moisturizers in order to minimize skin irritation associated with the anti-acne agent.

U.S. Pat. No. 4,056,611 discloses the use of benzoyl peroxide for the treatment of acne. The compositions also contain a surface active agent, an alkyl alcohol and water.

U.S. Pat. No. 4,105,782 discloses the use of amide and/or ammonium salts of $\alpha$- and $\beta$-hydroxy acids and $\alpha$-keto acids for the treatment of acne. The acne treatment compounds disclosed in the '782 patent include the amide and/or ammonium salts of citric acid, glycolic acid, glucuronic acid, galacturonic acid, glucuronolactone, gluconolactone, $\alpha$-hydroxybutyric acid, $\alpha$-hydroxyisobutyric acid, malic acid, mandelic acid, pyruvic acid and several others.

U. S. Pat. No. 4,923,900 discloses compositions containing benzoyl peroxide, water and a water miscible solvent having a boiling point greater than that of water. Dimethylisosorbide is disclosed as a particularly preferred solvent in the disclosed compositions. The disclosed compositions are said to be useful for the treatment of skin conditions such as acne and seborrhea, dermatophyte infection, reactions to irritative plant contactants such as the oleoresins of poison ivy, and development offensive body odor.

PanOxyl Bar® is a commercial product that is known for the treatment of acne. In addition to containing benzoyl peroxide, it also contains cetearyl alcohol, cocamidopropyl betaine, corn starch, glycerin, hydrogenated castor oil, lactic acid, mineral oil, optical brighteners, PEG-14M, potassium lauryl sulfate, potassium phosphate, silica, sodium lauryl sulfate, sodium sulfate, titanium dioxide and water. The consistency of PanOxyl Bar® is similar to that of bar soap.

None of the compositions of the aforementioned references provide a benzoyl peroxide composition which combines the desired anti-acne properties with the desired non-irritating properties in a cream-like formulation.

Accordingly, an object of the present invention is to provide a stable topical composition for the treatment of acne that is less irritating or is perceived to be less irritating than topical anti-acne compositions in the prior art.

A further object of the present invention is to provide a method for treating acne by applying to the affected areas of a patient's skin a topical anti-acne composition that is less irritating or perceived to be less irritating than compositions in the prior art.

SUMMARY OF THE INVENTION

The present invention is directed towards a topical composition for the treatment of acne comprising water, an organic peroxide, an alpha hydroxy acid, a moisturizer, an isosorbide and a detergent. This invention also is directed towards a method of making the composition of this invention. The method involves (1) heating water to between 60° C. and 70° C.; (2) adding a detergent base to the water and mixing the solution; (3) cooling the solution and adding an alpha hydroxy acid, an isosorbide and sodium pyrollidone carboxylate; (4) continuing to cool the solution to between 25° C. and 35° C. and then adding benzoyl peroxide and a preservative to the solution; (5) mixing and milling the product until smooth; and (6) adjusting the pH of the product to a pH of 3–5 with a base. This invention also is directed towards a method for treating a patient afflicted with acne by applying the composition of this invention to the affected areas of the patient's skin.

DETAILED DESCRIPTION OF THE PREFERRED EMBODIMENTS

Benzoyl peroxide is a strong oxidizing agent which may be used in topical compositions for treating acne. However, when applied at concentrations that are effective for treating acne, benzoyl peroxide also may be irritating to the skin. Consequently, many compositions that contain benzoyl peroxide also include one or more moisturizers. Unfortunately, moisturizers often interfere with benzoyl peroxide's ability to be in contact with the skin, and thereby reduce its effectiveness in treating acne. This often occurs with oil-based moisturizers, such as isopropyl myristate, mineral oil or petrolatum.

The present invention is based in part on the use of more water-soluble moisturizers in combination with benzoyl peroxide. These moisturizers, such as, for example, dimethyl isosorbide and sodium pyrollidone carboxylate, reduce skin irritation associated with benzoyl peroxide but do not significantly reduce benzoyl peroxide's effectiveness in treating acne. Without wishing to be bound by theory, it is believed that these more water-soluble moisturizers may assist in solubilizing benzoyl peroxide in water without interfering with benzoyl peroxide's ability to be in contact with the skin.

Surprisingly, the present inventors have found that when combined with benzoyl peroxide in a pharmaceutically acceptable carrier, sodium pyrollidone carboxylate may be used alone or in combination with an alpha hydroxy acid (e.g., glycolic acid) or an alkyl ester of isosorbide (e.g., dimethyl isosorbide) to produce a topical acne treatment composition with reduced irritation, desirable foaming, and appropriate chemical and physical stability.

The topical compositions of the present invention include water, an organic peroxide, an alpha hydroxy acid, a moisturizer, an isosorbide and a detergent. The amount of water present in the compositions of this invention may be from about 30 weight percent to about 70 weight percent, based upon the weight of the composition.

Preferably, the amount of water present is from about 35 weight percent to about 55 weight percent.

Organic peroxides which may be included in the topical compositions of the present invention include any pharmaceutically acceptable organic peroxide, such as, for example, benzoyl peroxide, lauroyl peroxide, and carbamide peroxide. Preferably, the organic peroxide is benzoyl peroxide. The amount of organic peroxide present in the compositions of the invention may be from about 1 weight percent to about 20 weight percent, based upon the weight of the composition. Preferably, the organic peroxide is present in an amount from about 2.5 weight percent to about 10 weight percent.

Alpha hydroxy acids which may be included in the topical compositions of the present invention include any pharmaceutically acceptable alpha hydroxy acid, such as, for example, glycolic acid, lactic acid, 2-hydroxydecanoic acid, 2-hydroxystearic acid and malic acid. Preferably, the alpha hydroxy acid is one that is commonly used in topical compositions for treating acne, such as glycolic acid or lactic acid. Most preferably, the alpha hydroxy acid is glycolic acid. The amount of alpha hydroxy acid present in the compositions of the invention may be from about 0.1 weight percent to about 15 weight percent, based upon the weight of the composition. Preferably, the alpha hydroxy acid is present in an amount from about 1 weight percent to about 10 weight percent.

Moisturizers which may be included in the topical compositions of the present invention include any pharmaceutically acceptable moisturizer, such as, for example, sodium pyrollidone carboxylate, glycerin, glycolic acid, propylene glycol and sorbitol. Preferably, the moisturizer is sodium pyrollidone carboxylate. The amount of moisturizer present in the compositions of the invention may be from about 0.5 weight percent to about 20 weight percent, based upon the weight of the composition. Preferably, the moisturizer is present in an amount from about 1 weight percent to about 10 weight percent.

Isosorbides which may be included in the topical compositions of the present invention include any pharmaceutically acceptable isosorbide. Such isosorbides include, for example, dimethyl isosorbide, diethyl isosorbide, and ethylmethyl isosorbide. Preferably, the isosorbide is an alkyl ester of isosorbide, such as dimethyl isosorbide. The amount of isosorbide present in the compositions of the invention may be from about 0.05 weight percent to about 20 weight percent, based upon the weight of the composition. Preferably, the isosorbide is present in an amount from about 0.05 weight percent to about 10 weight percent.

Detergents which may be included in the topical compositions of the present invention include any pharmaceutically acceptable detergent. Such detergents include, for example, sodium potassium lauryl sulfate, cocamidopropyl betaine, sodium cocoylisethionate, and disodium cocoamphopropionate. Preferably, the detergent is sodium potassium lauryl sulfate or cocamidopropyl betaine. The amount of detergent present in the compositions of the invention may be from about 15 weight percent to about 60 weight percent, based upon the weight of the composition. Preferably, the detergent is present in an amount from about 25 weight percent to about 40 weight percent.

The compositions of the present invention also may contain various other ingredients that are commonly included in topical pharmaceutical compositions. Such ingredients include, for example, thickeners, preservatives, binders, wetting agents, bases and opacifiers.

Thickeners which may be included in the topical compositions of the present invention include any pharmaceutically acceptable thickener. Such thickeners include, for example, cetostearyl alcohol, corn starch, polyethylene glycol, PEG-14M (PEG-14M is available from Amerchol Corp., Edison, N.J.), xanthan gum, and magnesium aluminum silicate. The thickeners may be present in the compositions of the invention in an amount from about 1 weight percent to about 30 weight percent, based upon the weight of the composition. Preferably, the thickener is present in an amount from about 2 weight percent to about 25 weight percent.

Preservatives which may be included in the topical compositions of the present invention include any pharmaceutically acceptable preservative. Such preservatives include, for example, methylparaben, propylparaben, imidurea, and quatemium-15. Preferably, the preservative is methylparaben or imidurea. The amount of preservatives present in the compositions of the invention may be from about 0.05 weight percent to about 1 weight percent, based upon the weight of the composition. Preferably, the preservatives are present in an amount from about 0.1 weight percent to about 0.7 weight percent.

Binders which may be included in the topical compositions of the present invention include any pharmaceutically acceptable binder. Such binders include, for example, hydrogenated castor oil, starch, and microcrystalline cellulose. Preferably, the binder is hydrogenated castor oil. The amount of binder that may be present in the compositions of the invention may be from about 0.05 weight percent to about 20 weight percent, based upon the weight of the composition. Preferably, the binder is present in an amount from about 1 weight percent to about 15 weight percent.

Wetting agents which may be included in the topical compositions of the present invention include any pharmaceutically acceptable wetting agent. Such wetting agents include, for example, mineral oil, castor oil, and olive oil. Preferably, the wetting agent is mineral oil. The amount of wetting agent present in the compositions of the invention may be from about 0.05 weight percent to about 10 weight percent, based upon the weight of the composition. Preferably, the wetting agent is present in an amount from about 0.1 weight percent to about 5 weight percent.

Bases which may be included in the topical compositions of the present invention include any pharmaceutically acceptable base. Such bases include, for example, sodium hydroxide, sodium citrate, sodium acetate, sodium phosphate, and sodium lactate.

Preferably, the base is sodium hydroxide. The amount of base present in the compositions of the invention may be from about 0.1 weight percent to about 5 weight percent, based upon the weight of the composition, depending upon the strength of the base. Preferably, the base is present in an amount from about 0.5 weight percent to about 3 weight percent.

Opacifiers which may be included in the topical compositions of the present invention include any pharmaceutically acceptable opacifier. Such opacifiers include, for example, titanium dioxide, zinc oxide, and magnesium stearate. Preferably, the opacifier is titanium dioxide. The amount of opacifier present in the compositions of the invention may be from about 0.05 weight percent to about 5 weight percent, based upon the weight of the composition. Preferably, the opacifier is present in an amount from about 0.1 weight percent to about 3 weight percent.

The topical composition of the present invention may be made by the following process: (1) adding water to a vessel and heating the water to between 60° C. to 70° C.; (2) while mixing, add and disperse the detergent base; (3) allow the solution to cool, and while the solution is cooling, add and disperse the alpha hydroxy acid (i.e., glycolic acid and/or lactic acid), isosorbide, and Sodium Pyrollidone Carboxylate; (4) when the temperature of the solution reaches 25° C. to 35° C., add and disperse with constant mixing the preservative (i.e., imidurea and/or methylparaben) and the benzoyl peroxide; (5) mix and mill the suspension as necessary to produce a smooth product; and (6) adjust the pH of the product to a pH of 3–5 with sodium hydroxide, if necessary.

The examples which follow are intended as illustrations of certain preferred embodiments of the invention, and no limitation of the invention is implied.

EXAMPLE 1

A benzoyl peroxide creamy wash according to the invention was prepared by the following procedure. The water was placed into a suitable vessel and heated to between 60° C. and 70° C. The detergent base (Tensianol 399 KS-1) was added to the water while the water was stirred. The resultant solution was then allowed to cool. While the solution was cooling, the glycolic acid, dimethyl isosorbide, and sodium pyrollidone carboxylate were added to the solution while stirring was continued. When the temperature of the solution fell to between 25° C. and 35° C., the imidurea, methylparaben and benzoyl peroxide were added to the solution, and stirring was continued. The resultant suspension was mixed and passed through a Gaulin Homogenizer until a smooth product with a mean particulate particle size of less than 60 microns was obtained. The pH of the product was then adjusted with sodium hydroxide to a pH of 3–5.

| Ingredients | % W/W |
| --- | --- |
| Benzoyl Peroxide Hydrous | 5.87 |
| Dimethyl Isosorbide | 0.100 |
| Glycolic Acid | 0.35 |
| Imidurea | 0.500 |
| Methylparaben | 0.100 |
| Purified Water | 50.22 |
| Sodium Hydroxide | 0.100 |
| Sodium Pyrollidone Carboxylate | 1.00 |
| Tensianol 399 KS-1 | 41.76 |
|  | 100.00 |

EXAMPLE 2

The following benzoyl peroxide creamy wash is prepared in accordance with the procedures set forth in Example 1.

| Ingredients | % W/W | |
| --- | --- | --- |
| Benzoyl Peroxide Hydrous | 2.50 | |
| Dimethyl Isosorbide | 0.100 | |
| Glycolic Acid | 2.00 | |
| Imidurea | 0.500 | |
| Methylparaben | 0.100 | |
| Purified Water  q.s. to 100 ml | 39.80 | (approx.) |
| Sodium Hydroxide | q.s. to pH of 3–5 | |
| Sodium Pyrollidone Carboxylate | 10.00 | |
| Tensianol 399 KS-1 | 45.00 | |
|  | 100.00 | |

EXAMPLE 3

The following benzoyl peroxide creamy wash is prepared in accordance with the procedures set forth in Example 1.

The lactic acid is added along with the glycolic acid.

| Ingredients | % W/W | |
|---|---|---|
| Benzoyl Peroxide Hydrous | 5.00 | |
| Dimethyl Isosorbide | 1.00 | |
| Glycolic Acid | 1.00 | |
| Lactic Acid | 1.00 | |
| Imidurea | 0.500 | |
| Methylparaben | 0.100 | |
| Purified Water q.s. to 100 ml | 53.40 | (approx.) |
| Sodium Hydroxide | q.s. to pH of 3–5 | |
| Sodium Pyrollidone Carboxylate | 3.00 | |
| Tensianol 399 KS-1 | 35.00 | |
| | 100.00 | |

EXAMPLE 4

The following benzoyl peroxide creamy wash is prepared in accordance with the procedures set forth in Example 1. The lactic acid is added at the point were the glyolic acid is added in Example 1.

| Ingredients | % W/W | |
|---|---|---|
| Benzoyl Peroxide Hydrous | 7.50 | |
| Dimethyl Isosorbide | 5.00 | |
| Lactic Acid | 5.00 | |
| Imidurea | 0.50 | |
| Methylparaben | 0.10 | |
| Purified Water q.s. to 100 ml | 39.40 | (approx.) |
| Sodium Hydroxide | q.s. to pH of 3–5 | |
| Sodium Pyrollidone Carboxylate | 5.00 | |
| Tensianol 399 KS-1 | 37.50 | |
| | 100.00 | |

EXAMPLE 5

The following benzoyl peroxide creamy wash is prepared in accordance with the procedures set forth in Example 1. The lactic acid is added at the point were the glyolic acid is added in Example 1.

| Ingredients | % W/W | |
|---|---|---|
| Benzoyl Peroxide Hydrous | 10.00 | |
| Dimethyl Isosorbide | 10.00 | |
| Lactic Acid | 10.00 | |
| Imidurea | 0.50 | |
| Methylparaben | 0.10 | |
| Purified Water q.s. to 100 ml | 37.40 | (approx.) |
| Sodium Hydroxide | q.s. to pH of 3–5 | |
| Sodium Pyrollidone Carboxylate | 2.00 | |
| Tensianol 399 KS-1 | 30.00 | |
| | 100.00 | |

Tensianol 399 KS-1, which is available from Uniqema, Inc., Wilmington, Del. contains cetostearyl alcohol, cocamidopropyl betaine, corn starch, glycerin, hydrogenated castor oil, mineral oil, PEG-14M, sodium potassium lauryl sulfate, and titanium dioxide.

TABLE 1A

Stability data for a 254.1 Kg batch of a composition of the invention. The initial amount of benzoyl peroxide present in the composition was 4.66%. Samples were taken from the BOTTOM of the batch.

| Storage Temp (° C.) | Time Stored (days) | % Benzoyl Peroxide | % of initial amount of benzoyl peroxide |
|---|---|---|---|
| 25 | 30 | 4.72 | 101.2 |
| 25 | 60 | 4.79 | 102.8 |
| 25 | 91 | 4.74 | 101.7 |
| 25 | 182 | 4.77 | 102.4 |
| 30 | 30 | 4.63 | 99.4 |
| 30 | 60 | 4.61 | 98.9 |
| 30 | 91 | 4.67 | 100.2 |
| 30 | 182 | 4.27 | 91.6 |
| 40 | 30 | 4.24 | 91.0 |
| 40 | 60 | 3.79 | 81.3 |
| 40 | 91 | 3.25 | 69.7 |
| 40 | 182 | 1.81 | 38.8 |

TABLE 1B

Stability data for the 254.1 Kg batch of a composition of the invention shown in Example 1A. Samples were taken from the TOP of the batch.

| Storage Temp (° C.) | Time Stored (days) | % Benzoyl Peroxide | % of initial amount of Benzoyl Peroxide |
|---|---|---|---|
| 25 | 30 | 4.62 | 99.1 |
| 25 | 60 | 4.61 | 98.9 |
| 25 | 91 | 4.64 | 99.6 |
| 25 | 182 | 4.54 | 97.4 |
| 30 | 30 | 4.59 | 98.5 |
| 30 | 60 | 4.60 | 98.7 |
| 30 | 91 | 4.54 | 97.4 |
| 30 | 182 | 4.32 | 92.7 |
| 40 | 30 | 4.19 | 89.9 |
| 40 | 60 | 3.68 | 79.0 |
| 40 | 91 | 3.14 | 67.4 |
| 40 | 182 | 0.88 | 18.9 |

As shown in Tables 1A and 1B, a composition according to the invention having an initial amount of benzoyl peroxide of about 4.5% showed good stability with respect to the benzoyl peroxide component at temperatures of 25° C. and 30° C. for at least about days. At 40° C. the composition showed acceptable stability (i.e., at least about 90% of the initial amount of benzoyl peroxide) for 30 days, but significant degradation (i.e., more than about 10%) when maintained at 40° C. for 60 days or more.

TABLE 2A

Stability data for a 253.5 Kg batch of a composition of the invention. The initial amount of benzoyl peroxide present in the composition was 9.04%. Samples were taken from the BOTTOM of the batch.

| Storage Temp (° C.) | Time Stored (days) | % Benzoyl Peroxide | % of initial amount of Benzoyl Peroxide |
|---|---|---|---|
| 25 | 30 | 9.22 | 102.0 |
| 25 | 60 | 9.30 | 102.9 |
| 25 | 91 | 9.23 | 102.1 |
| 25 | 182 | 9.46 | 104.6 |
| 30 | 30 | 9.14 | 101.1 |
| 30 | 60 | 9.29 | 102.8 |
| 30 | 91 | 9.19 | 101.6 |
| 30 | 182 | 8.83 | 97.7 |
| 40 | 30 | 8.54 | 94.5 |
| 40 | 60 | 8.39 | 92.8 |

TABLE 2A-continued

Stability data for a 253.5 Kg batch of a composition of the invention. The initial amount of benzoyl peroxide present in the composition was 9.04%. Samples were taken from the BOTTOM of the batch.

| Storage Temp (° C.) | Time Stored (days) | % Benzoyl Peroxide | % of initial amount of Benzoyl Peroxide |
|---|---|---|---|
| 40 | 91 | 8.47 | 93.7 |
| 40 | 182 | 7.17 | 79.3 |

TABLE 2B

Stability data for the 253.5 Kg batch of a composition of the invention shown in Example 1A. Samples were taken from the TOP of the batch.

| Storage Temp (° C.) | Time Stored (days) | % Benzoyl Peroxide | % of initial amount of Benzoyl Peroxide |
|---|---|---|---|
| 25 | 30 | 8.87 | 98.1 |
| 25 | 60 | 8.98 | 99.3 |
| 25 | 91 | 9.12 | 100.9 |
| 25 | 182 | 8.83 | 97.7 |
| 30 | 30 | 8.78 | 97.1 |
| 30 | 60 | 8.87 | 98.1 |
| 30 | 91 | 8.73 | 96.6 |
| 30 | 182 | 8.42 | 93.1 |
| 40 | 30 | 8.62 | 95.4 |
| 40 | 60 | 8.24 | 91.2 |
| 40 | 91 | 7.64 | 84.5 |
| 40 | 182 | 4.94 | 54.6 |

As shown in Tables 2A and 2B, a composition according to the invention having initial amount of benzoyl peroxide of about 9.0% showed good stability with respect to the benzoyl peroxide component at temperatures of 25° C. and 30° C. for at least about days. At 40° C. the composition showed acceptable stability for at least 60 days, but significant degradation when maintained at 40° C. for 90 days or more.

Accordingly, it will be understood that the preferred embodiments of the invention have been disclosed by way of example and that other modifications and alterations may occur to those skilled in the art without departing from the scope and spirit of the appended claims.

What is claimed is:

1. A topical composition for the treatment of acne consisting essentially of:
   (a) water present in an amount from about 25% by weight to about 60% by weight of the composition;
   (b) benzoyl peroxide present in an amount from about 1.0% by weight to about 20.0% by weight of the composition;
   (c) an alpha hydroxy acid selected from the group consisting of glycolic acid, lactic acid, 2-hydroxydecanoic acid, malic acid and mixtures thereof and present in an amount from about 0,1% by weight to about 15% by weight of the composition;
   (d) a moisturizer selected from the group consisting of sodium pyrollidone carboxylate, glycerin, propylene glycol, sorbitol and mixtures thereof and present in an amount from about 0.1% by weight to about 10% by weight of the composition;
   (e) an alkyl ester of isosorbide selected from the group consisting of dimethyl isosorbide, diethyl isosorbide, dipropyl isosorbide, ethylmethyl isosorbide and mixtures thereof and present in an amount from about 0.05% by weight to about 10% by weight of the composition; and
   (f) a detergent selected from the group consisting of cocamidopropyl betaine, sodium potassium lauryl sulfate, sodium cocoylisethionate, disodium cocoamphopropionate and mixtures thereof and present in an amount from about 15% by weight to about 60% by weight of the composition.

2. The composition according to claim 1, wherein said benzoyl peroxide is present in an amount from about 2.5% by weight to about 10.0% by weight of the composition.

3. The composition according to claim 1, wherein said alpha hydroxy acid is present in an amount from about 0.1% by weight to about 10% by weight of the composition.

4. The composition according to claim 1, wherein said alpha hydroxy acid is glycolic acid.

5. The composition according to claim 1, wherein said alpha hydroxy acid is lactic acid.

6. The composition according to claim 1, wherein said moisturizer is present in an amount from about 0.5% by weight to about 5% by weight of the composition.

7. The composition according to claim 1, wherein said moistuirizer is sodium pyrollidone carboxylate.

8. The composition according to claim 1, wherein said alkyl ester of isosorbide is present in an amount from about 0.05% by weight to about 5% by weight of the composition.

9. The composition according to claim 8, wherein said alkyl ester of isosorbide is dimethyl isosorbide.

10. The composition according to claim 1, wherein said detergent is present in an amount from about 25% by weight to about 40% by weight of the composition.

11. The composition according to claim 10, wherein said detergent is a mixture of cocainidopropyl betaine and sodium potassium lauryl sulfate.

12. The composition according to claim 10, wherein said detergent is sodium potassium lauryl sulfate.

13. The composition according to claim 1, wherein said water is present in an amount from about 30% by weight to about 55% by weight of the composition.

14. The composition according to claim 1, further comprising at least one thickener selected from the group consisting of cetostearyl alcohol, corn starch, polyethylene glycol, polyethylene, xanthan gut, magnesium aluminum silicate and mixtures thereof.

15. The composition according to claim 14, further comprising at least one preservative selected from the group consisting of methylparaben, propylparaben, imidurea, butyl paraben, azolidinyl urea, quaternium-15 and mixtures thereof.

16. The composition according to claim 15, further comprising a binder.

17. The composition according to claim 16, further comprising a wetting agent.

18. The composition according to claim 17, further comprising a base.

19. The composition according to claim 18, further comprising an opacifier.

20. A method for treating a person afflicted with acne which comprises applying to an affected area of the person's skin a therapeutically effective amount of a composition consisting essentially of:
   (a) water;
   (b) benzoyl peroxide present in an amount from about 2.5% by weight to about 10.0% by weight of the composition;

(c) an alpha liydroxy acid selected from the group consisting of glycolic acid, lactic acid, 2-hydroxydecanoic acid, malic acid and mixtures thereof and present in an amount from about 0.1% by weight to about 10% by weight of the composition;

(d) a moisturizer selected from the group consisting of sodium pyrollidone carboxylate, glycerin, propylene glycol, sorbitol and mixtures thereof and present in an amount from about 0.1% by weight to about 10% by weight of the composition;

(e) an alkyl ester of isosorbide selected from the group consisting of dimethyl isosorbide, dictliyl isosorbide, dipropyl isosorbide, ethylmethyl isosorbide and mixtures thereof and present in an amount from about 0.05% by weight to about 10% by weight of the composition; and (f) a detergent selected from the group consisting of cocamidopropyl betaine, sodium potassium lauryl sulfate, sodium cocoylisethionate, disodium cocoaniphopropionate and mixtures thereof and present in an amount from about 15% by weight to about 60% by weight of the composition.

* * * * *